US008961583B2

(12) United States Patent
Hojeibane et al.

(10) Patent No.: US 8,961,583 B2
(45) Date of Patent: Feb. 24, 2015

(54) OPTIMIZED FLEX LINK FOR EXPANDABLE STENT

(75) Inventors: Hikmat Hojeibane, Princeton, NJ (US); David Christopher Majercak, Stewartsville, NJ (US); Volker Niermann, Bound Brook, NJ (US)

(73) Assignee: Cordis Corporation

( * ) Notice: Subject to any disclaimer, the term of this patent is extended or adjusted under 35 U.S.C. 154(b) by 1363 days.

(21) Appl. No.: 10/936,199

(22) Filed: Sep. 8, 2004

(65) Prior Publication Data

US 2007/0255391 A1 Nov. 1, 2007

(51) Int. Cl.
*A61F 2/06* (2013.01)
*A61F 2/915* (2013.01)
*A61F 2/91* (2013.01)

(52) U.S. Cl.
CPC . *A61F 2/915* (2013.01); *A61F 2/91* (2013.01); *A61F 2002/91541* (2013.01); *A61F 2002/91558* (2013.01); *A61F 2230/0054* (2013.01); *A61F 2230/0067* (2013.01)
USPC ........................................................ 623/1.15

(58) Field of Classification Search
CPC ............ A61F 2002/91541; A61F 2002/91558; A61F 2/915; A61F 2/91
USPC ............. 623/1.15, 1.16, 1.11, 1.2, 1.23, 1.42, 623/1.46, 1.27
See application file for complete search history.

(56) References Cited

U.S. PATENT DOCUMENTS

| 5,913,895 | A | * | 6/1999 | Burpee et al. ................... 623/1.2 |
| 6,033,433 | A | * | 3/2000 | Ehr et al. ....................... 623/1.16 |
| 6,217,608 | B1 | * | 4/2001 | Penn et al. ..................... 623/1.16 |
| 6,520,985 | B1 | | 2/2003 | Burpee et al. |
| 6,929,660 | B1 | * | 8/2005 | Ainsworth et al. ........... 623/1.15 |
| 6,979,349 | B1 | * | 12/2005 | Dang et al. .................... 623/1.15 |
| 7,179,288 | B2 | * | 2/2007 | Shanley ........................ 623/1.42 |
| 7,854,757 | B2 | | 12/2010 | Fleming |
| 2003/0004566 | A1 | | 1/2003 | Dang et al. |
| 2003/0014102 | A1 | * | 1/2003 | Hong et al. ................... 623/1.15 |
| 2003/0083731 | A1 | * | 5/2003 | Kramer et al. ................ 623/1.15 |
| 2004/0167610 | A1 | | 8/2004 | Fleming |

FOREIGN PATENT DOCUMENTS

EP 0806190 A1 11/1997
EP 0806190 * 12/1997 ................ A61F 2/06
(Continued)

OTHER PUBLICATIONS

International Search Report re: PCT/US2005/032168 dated Feb. 9, 2006.

(Continued)

*Primary Examiner* — Thomas McEvoy
*Assistant Examiner* — Julie A Szpira

(57) ABSTRACT

This invention relates generally to an expandable intraluminal medical device for use within a body passageway or duct, and more particularly to an optimized stent having flexible links that minimize foreshortening during stent deployment. In one embodiment of the present invention the intraluminal prosthetic device includes a first hoop section, a second hoop section, and one or more flex members attached between the first and the second hoop section. Each flex member comprises two generally longitudinally extending curved segments connected by a circumferentially undulating segment.

12 Claims, 8 Drawing Sheets

(56) References Cited

FOREIGN PATENT DOCUMENTS

| EP | 1179323 | 2/2002 |
| EP | 1346706 | 4/2010 |
| JP | 2002177400 | 8/2001 |
| JP | 2004255193 | 2/2004 |
| WO | 0213725 | 2/2002 |

OTHER PUBLICATIONS

Notification for Reasons for Refusal in Japanese Patent Application No. 2012-037277 dated May 7, 2013.

* cited by examiner

OPTIMIZED FLEX LINK FOR EXPANDABLE STENT

FIELD OF THE INVENTION

This invention relates generally to expandable intraluminal medical devices for use within a body passageway or duct, and more particularly to optimized stent flexible links that minimize foreshortening during stent deployment.

BACKGROUND OF THE INVENTION

The use of intraluminal prosthetic devices has been demonstrated to present an alternative to conventional vascular surgery. Intraluminal prosthetic devices are commonly used in the repair of aneurysms, as liners for vessels, or to provide mechanical support to prevent the collapse of stenosed or occluded vessels.

Intraluminal endovascular prosthetics involves the percutaneous insertion of a generally tubular prosthetic device, such as a stent, into a vessel or other tubular structure within the vascular system. The stent is typically delivered to a specific location inside the vascular system in a compressed state by a catheter. Once delivered to the desired location, the stent is deployed by expanding the stent into the vessel wall. The expanded stent typically has a diameter that is several times larger than the diameter of the stent in its compressed state. The expansion of the stent may be performed by several methods known in the art, such as by a mechanical expansion device (balloon catheter expansion stent) or by self-expansion.

The positioning of the stent within the vessel is a critical factor that affects the performance of the stent and the success of the medical procedure. Since the region in the vessel lumen at which the stent is to be deployed is usually very difficult for a physician to access, it is essential that the stent's deployed diameter and length be known before the physician can accurately position the correctly sized device.

Careful sizing of the correct stent for the desired region of the vessel lumen may be a difficult challenge for many physicians. Although the dimensions of the body vessel at the region may be known, uncertainty about the stent's exact deployed diameter and length may lead to less than optimal performance. One cause for uncertainty in the stent's deployed diameter and length is a condition known as foreshortening.

Foreshortening can be better understood by defining the condition within the context of change in the stent length before and after deployment. For the purpose of this definition, "crimped length" describes the starting point of the stent—that is the length of the unexpanded stent mounted on a delivery catheter prior to deployment. The term "deployed length" is defined at the clinical end point of change—that is the length of the stent deployed within the lumen. Foreshortening is equivalent to the distance between these two points, i.e. the difference between the contained ("crimped") and deployed length.

Foreshortening occurs to varying degrees with all stents. This is especially true for endovascular stents greater than 4 millimeters in diameter. The amount of stent foreshortening is determined predominately by how the particular stent design accommodates expansion. For example, self-expanding stents are commonly deployed by operation of a retractable sheath. As the sheath is retracted the distal end of the stent is released first. Foreshortening can occur within this distal segment until the stent anchors on the lumen wall. As the sheath retraction continues, the proximal segment will foreshorten as it is deployed.

Balloon-expandable stents also foreshorten during expansion. Stents deployed by standard catheter balloons invariably see the balloon inflate at the weakest section first. Typically, the weakest section of the balloon will be at the exposed distal and/or proximal ends, i.e. the sections of the balloon not supported directly by the catheter or the stent. Accordingly, as the balloon is expanded the proximal end and/or distal end(s) of the balloon will inflate first. The inflated end(s) of the stent will experience the pressure of the balloon pressing outward in a radial direction to expand the stent, and also inwardly in an axial compressive direction. This axial compressive force causes the weaker connecting links or "flex links" of the stent to compress, causing the stent to foreshorten.

What is needed is an intraluminal medical device that will accommodate the device expansion into the wall of the lumen, while minimizing device foreshortening.

SUMMARY OF THE INVENTION

This invention relates generally to expandable intraluminal medical devices for use within a body passageway or duct, and more particularly to a stent having optimized flexible members between adjacent hoop structures that minimize foreshortening during stent deployment.

In one embodiment of the present invention the intraluminal prosthetic device comprises a first hoop section, a second hoop section and a plurality of flex members. Each flex member has a first and a second end, wherein the first end of each flex member is attached to the first hoop section and the second end of each flex member is attached to the second hoop section. The flex members further comprise at least two generally longitudinally extending curved segments connected by a circumferentially undulating segment.

In another embodiment of the present invention, the intraluminal prosthetic device comprises a first hoop section, a second hoop section, and one or more undulating flex members attached between the first and the second hoop section. Each flex member comprises two generally longitudinally extending curved segments connected by a circumferentially undulating segment.

DETAILED DESCRIPTION OF THE INVENTION

Figure 1:
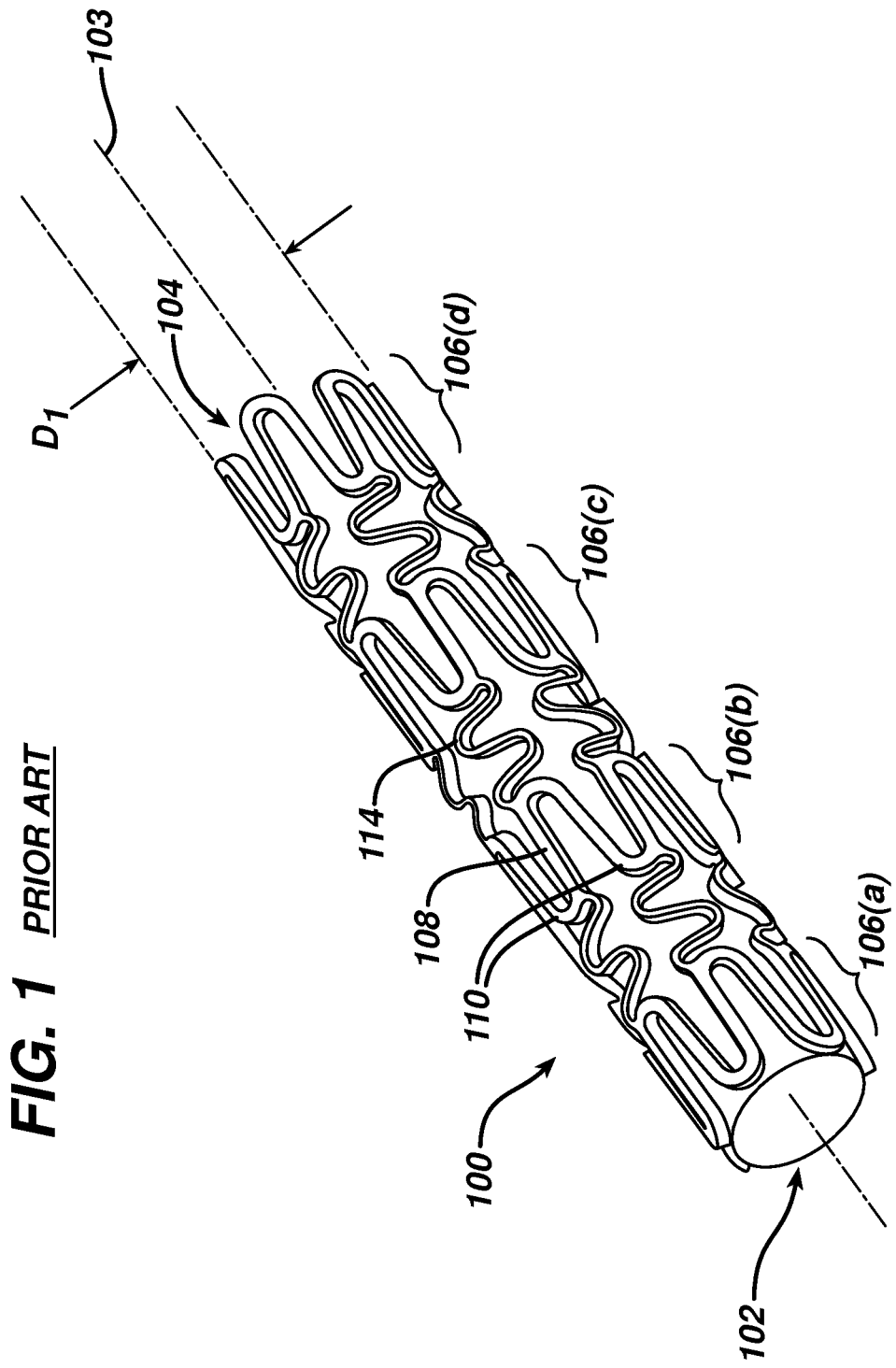
FIG. 1 illustrates a perspective view of an exemplary stent in an unexpanded or crimped, pre-deployed state.

The present invention describes a flexible component of an intraluminal medical device that will accommodate the device expansion into the wall of a vessel lumen, while minimizing foreshortening of the device caused by axial compression of the device components. An intravascular stent will be described for the purpose of example. However, as the term is used herein, intraluminal medical device includes but is not limited to any expandable intravascular prosthesis, expandable intraluminal vascular graft, stent, or any other mechanical scaffolding device used to maintain or expand a body passageway. Further, in this regard, the term "body passageway" encompasses any duct within a mammalian's body, or any body vessel including but not limited to any vein, artery, duct, vessel, passageway, trachea, ureters, esophagus, as well as any artificial vessel such as grafts.

The flexible component according to the present invention may be incorporated into any radially expandable stent, including self-expanding stents and mechanically expanded stents. Mechanically expanded stents include, but are not limited to stents that are radially expanded by an expansion member, such as by the expansion of a balloon.

With reference to the drawing figures, like parts are represented by like reference numerals throughout the various different figures. By way of example, strut 108 in FIG. 1 is equivalent to strut 308 in FIG. 3.

Figure 2:
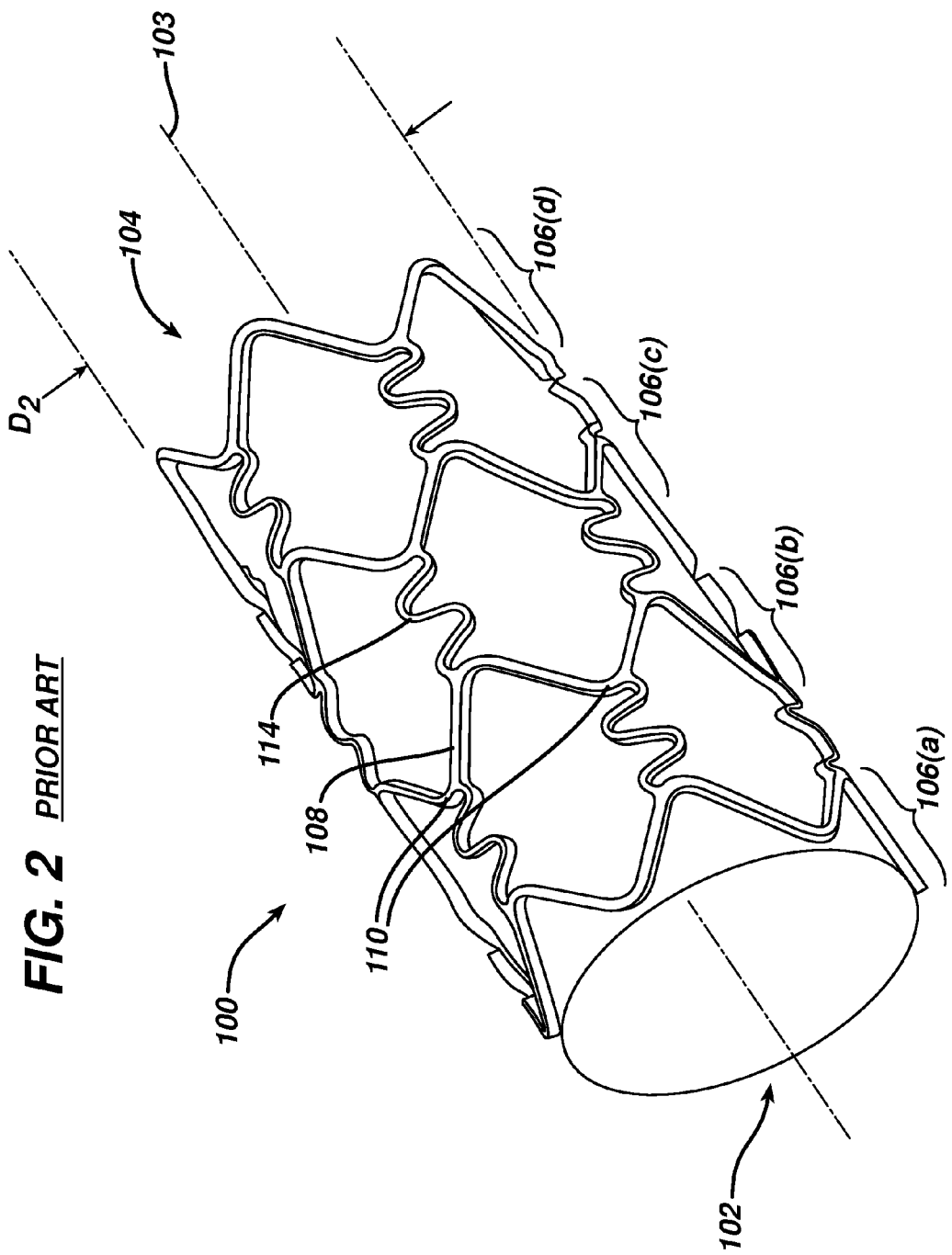
FIG. 2 illustrates a perspective view of an exemplary stent in an expanded, deployed state.
Figure 3:
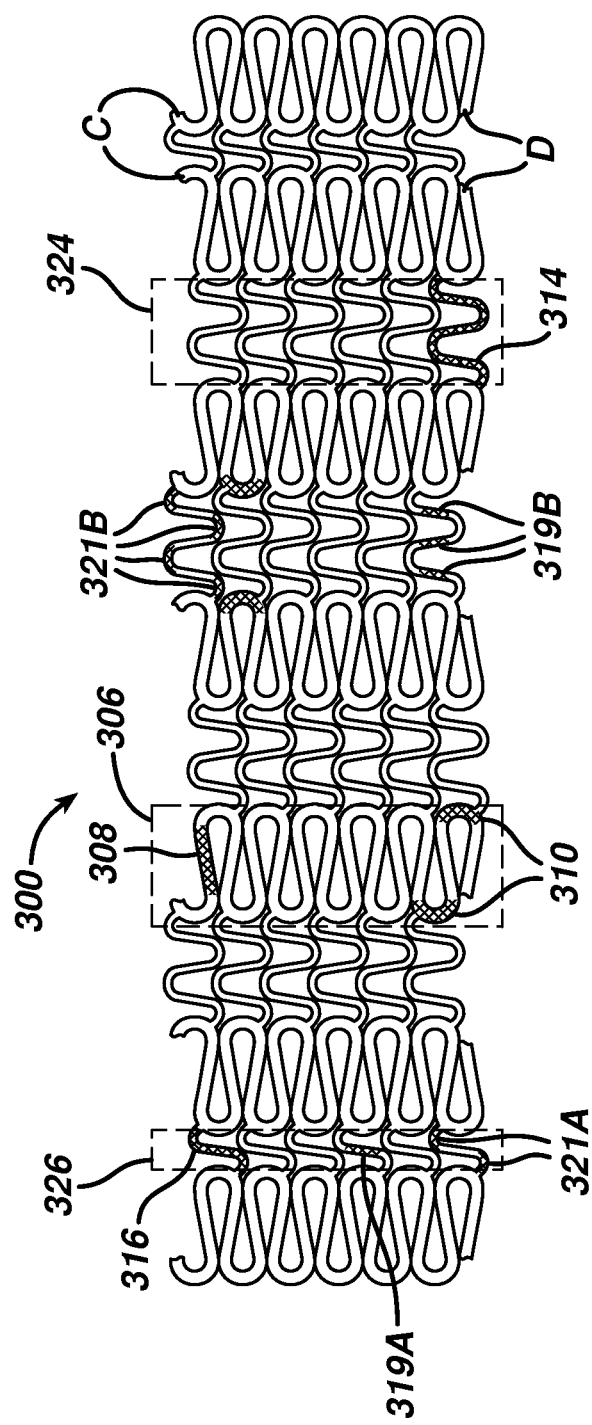
FIG. 3 illustrates a two-dimensional view of an exemplary stent in its crimped, pre-deployed configuration, as it would appear if it were cut longitudinally and then laid out flat.
Figure 4A:
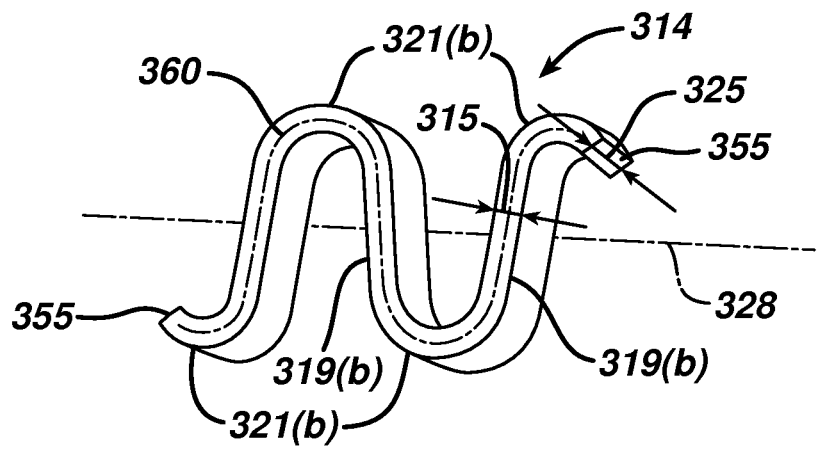
FIG. 4A illustrates a perspective view of an exemplary prior art "N" flex link.
Figure 4B:
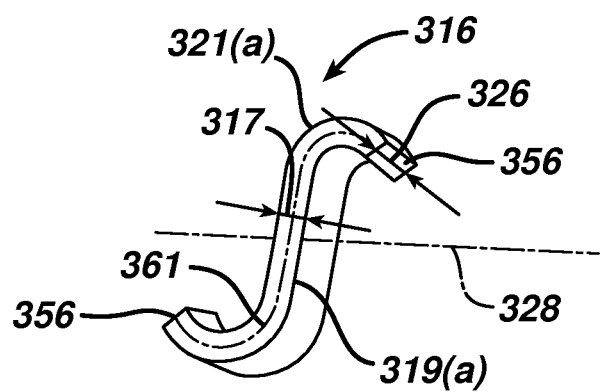
FIG. 4B illustrates a perspective view of an exemplary prior art "J" flex link.
Figure 5:
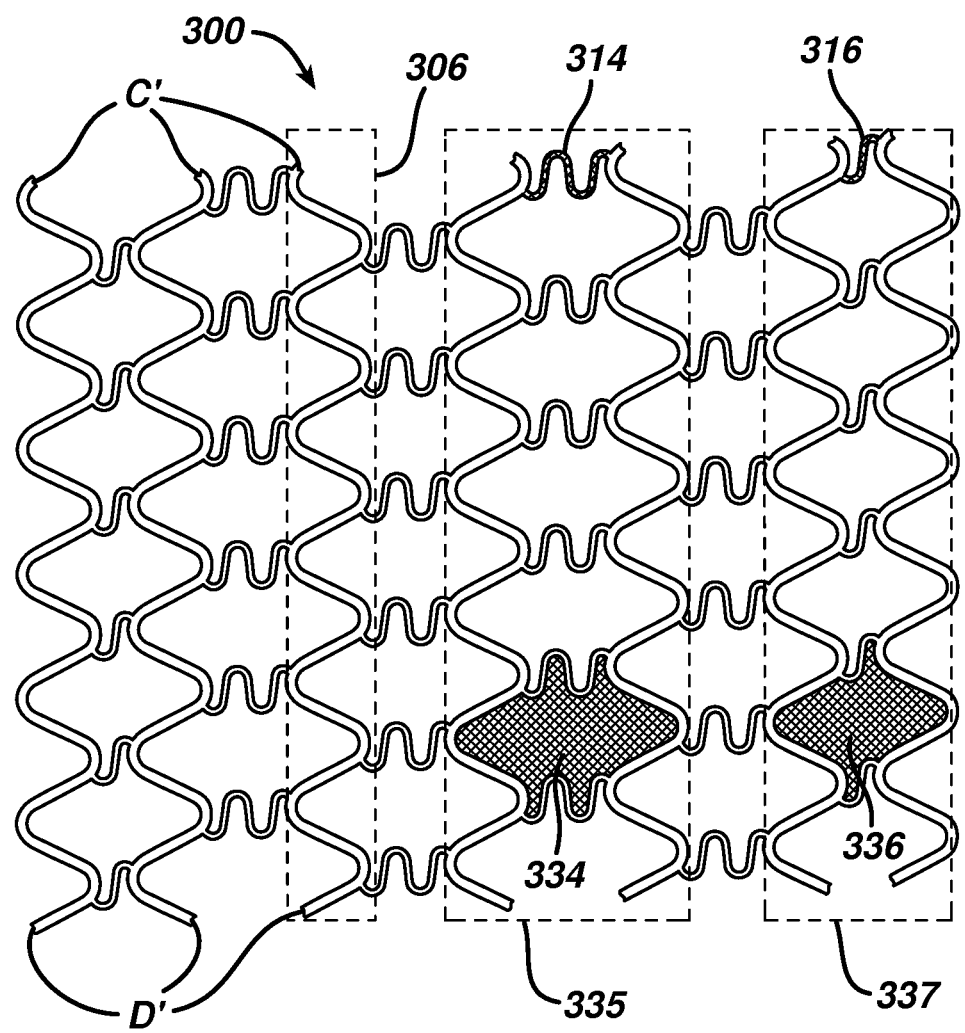
FIG. 5 illustrates a two-dimensional view of an exemplary stent in its expanded, deployed configuration as it would appear if it were cut longitudinally and then laid out flat.

Referring to FIGS. 1-5, there are illustrated exemplary stents 100, 300 as are known in the art. FIGS. 1 and 3 illustrate typical prior art stents 100, 300 in an unexpanded or crimped, pre-deployed state, while FIGS. 2 and 5 show the stents 100, 300 in the fully expanded state. Although Z or S shaped pattern stents are shown for the purpose of example, the illustration is not to be construed as limiting the scope of this invention.

Turning now to FIGS. 1 and 2, a stent 100 comprises a tubular configuration of structural elements having proximal and distal open ends 102, 104 and defining a longitudinal axis 103 extending there between. The stent 100 has a first diameter D1 for insertion into a patient and navigation through the vessels, and a second diameter D2 for deployment into the target area of a vessel, with the second diameter being greater than the first diameter.

The stent 100 structure comprises a plurality of adjacent hoops 106(a)-(d) extending between the proximal and distal ends 102, 104. The hoops 106(a)-(d) include a plurality of longitudinally arranged strut members 108 and a plurality of loop members 110 connecting adjacent struts 108. Adjacent struts 108 are connected at opposite ends in a substantially S or Z shaped pattern so as to form a plurality of cells. However, one of ordinary skill in the art would recognize that the pattern shaped by the struts is not a limiting factor in this invention, and other shaped patterns may be used. The plurality of loops 110 have a substantially semi-circular configuration and are substantially symmetric about their centers.

The stent 100 structure further comprises a plurality of bridge members or flex links 114, which connect adjacent hoops 106(a)-(d). Each flex link 114 comprises two ends. Each one end of each flex link 114 is attached to one loop 110 on one hoop, for example hoop 106(c), and the other end of each flex link 114 is attached to one loop 110 on an adjacent hoop, for example hoop 106(d). The flex links 114 connect adjacent hoops 106(a)-(d) together at flex link to loop connection regions.

The Figures generally show a stent having a closed cell design, with the flex links 114 connected to the adjacent hoop 106 at each loop 110. In any of the described configurations, the connections between the hoop structures 106 and the adjacent flex link 114 may be made at every loop member 110; or alternatively, at a subset of the loop members 110 around the circumference of the hoop 106. In other words, the connected loop members 110 may alternate with unconnected loop members 110 in some defined pattern around the circumference of hoop section 106.

FIGS. 3 and 5 illustrate a typical stent 300 as is know in the prior art. As shown in FIG. 3, stent 300 is in its crimped, pre-deployed state, as it would appear if it were cut longitudinally and then laid out flat in a 2-dimensional configuration. Similarly, stent 300 in FIG. 5 is a 2-dimensional representation of the cylindrical stent 300 after deployment; i.e. after radially outward expansion. It should be clearly understood that the stent 300 depicted in FIGS. 3 and 5 is in fact cylindrical in shape, similar to stent 100 shown in FIG. 1, and is only shown in the flat configuration for the purpose of illustration. This cylindrical shape would be obtained by rolling the flat configuration of FIGS. 3 and 5 into a cylinder with the top points "C" joined to the bottom points "D". The stent 300 is typically fabricated by laser machining of a cylindrical, stainless steel tube.

A set of strut members (as shown within the dotted rectangle) form a closed, cylindrical, hoop section 306 of the stent 300, similar to hoop 106(c) of FIG. 1. As described earlier, the hoop section 306 comprises a plurality of loop members 310 connected by longitudinally arranged strut members 308. The hoop section 306 can be said to consist of a multiplicity of strut elements with each strut element consisting of one loop member 310 joined to one strut 308.

Except at the extreme ends of the stent 300, every curved loop member 310 in adjacent hoops 306 are attached to a flex link that is either an "N" flex link 314 or a "J" flex link 316. A stent 300 that is thus fully connected is called a "closed cell" stent. However other open and closed cell designs are also contemplated by the present invention such that every curved loop member 310 may not be attached to a flex link. For example, the connections between the hoop structures 306 and the adjacent flex link 314 may be made at every loop member 310; or alternatively, at a subset of the loop members 310 around the circumference of the hoop 306. In other words, the connected loop, members 310 may alternate with unconnected loop members 310 in some defined pattern around the circumference of hoop section 306.

FIG. 5 shows deployed structural cells 336 having two of the "J" flex links 316 on their perimeter, and deployed special expandable cells 334 having two of the flexible "N" flex links 314 on their perimeter. As noted above, circumferentially extending sets of cells are formed into hoop-like, circumferential cylindrical sections (hoop sections 306) with (in this case) exactly six cells per cylindrical segment. Typically a multi-cell stent would have at least three cells per hoop section. The stent 300 illustrated in FIGS. 3 and 5 has exactly two cylindrical hoops (illustrated in the flat as sections 337) of structural cells 336, and four cylindrical sections 335 of expandable cells 334.

Another way to describe the fully connected configuration of the stent 300 is as multiple longitudinally spaced sets of hoop sections 306 inter-connected by either sets of flexible "N" flex links 324 or sets of flexible "J" flex links 326. Each set of "N" flex links 324 comprises multiple circumferentially spaced "N" flex links 314 with each "N" flex link 314 being connected to two curved loop members 310 of adjacent hoop sections 306. The number of "N" flex links 314 in the set of "N" flex links 324 is no more than one-half of the total number of curved loop members 310 in the loop section 306.

Similarly, each set of flexible "J" flex links 326 consists of multiple circumferentially spaced "J" flex links 316 with each "J" flex link being connected to two curved loop members 310 of the hoop section 306. The number of "J" flex links 316 in the set of "J" flex links 326 is no more than one half of the total number of curved loop members 310 in the hoop section 306.

FIGS. 4A and 4B show 3-dimensional, perspective views of the "N" flex link 314 and the "J" flex link 316 of the stent 300 respectively. The "N" link 314 comprises four generally longitudinally extending curved segments 321(b) connected by three generally circumferentially extending segments 319(b) with each "N" flex link 314 having two ends that are attached to curved loop members 310 at attachment points 355. The "N" flex link 314 shown in FIG. 4A has a strut width 315 as measured in a direction that is generally along the surface of the stent that is smaller than the wall thickness 325 as measured in a radial direction from the stent's longitudinal axis 328. Also illustrated in FIG. 4A is the centerline length 360 of the N flex link 314. The centerline length is directly proportional to flexibility of the flex link.

The strut width 315 for a stent is typically less than 0.10 mm to provide good flexibility while the wall thickness 325 is typically greater than 0.10 mm to provide good stent radiopacity. Ideally the ratio of the width 315 to the thickness 325 is less than 1.0 and preferably less than 0.8. For a stent, the nominal strut width 315 would typically be 0.08 mm and the nominal wall thickness 325 is typically 0.12 mm.

The combination of thin strut width 315 and thick wall thickness 325 allows the "N" flex link 314 to easily lengthen and shorten for increased stent flexibility while making the "N" flex link 314 relatively stiff with respect to bulging inward into the lumen of the stent 300. This stiffness enhances the ability of the "N" flex link 314 to push outward against plaque in a coronary artery after the stent 300 is deployed. In addition it was thought that the thin width 315 of the "N" flex link 314 would allow the flex link 314 to stretch during stent expansion, reducing the foreshortening of the stent 300. However, this axial flexibility contributes to the stent foreshortening.

As illustrated in FIG. 4B, each "J" link 316 consists of two generally longitudinally extending curved segments 321(a) connected by a straight circumferential segment 319(a), with each "J" flex link 316 having two ends that are identically attached to curved loop members 310 at attachment points 356. The "J" flex link 316 shown in FIG. 4B has a strut width 317 as measured in a direction that is generally along the surface of the stent that is smaller than the wall thickness 326 as measured in a radial direction from the stent's longitudinal axis 328. Also illustrated in FIG. 4B is the centerline length 361 of the "J" flex link 316. The centerline length is directly proportional to the flexibility of the flex link.

As previously described, 'the stent 300 shown in FIGS. 3 and 5 can be said to have adjacent hoop sections 306 that are connected either by multiple "N" flex links 314 or by multiple "J" flex links 316. Each "N" flex link 314 is shaped so as to nest together into the adjacent "N" flex link 314 as is clearly illustrated in FIG. 3. "Nesting" is defined as having the top of a first flexible link inserted beyond the bottom of a second flexible link situated just above that first flexible link. Similarly, the bottom of the first flexible link is inserted just below the top of a third flexible link that is situated just below the first flexible link. Thus, a stent with nested individual flexible links has each individual flexible link nested into both adjacent flexible links; i.e., the flexible link directly below and the flexible link directly above that individual flexible link. This nesting permits crimping of the stent 300 to smaller diameters without having the "N" flex links 314 overlap.

Since stents similar to stent 300 are delivered percutaneously into a body lumen, the flex links are designed to allow stent 300 to bend with relative ease as it goes around curved arteries and vessels. To provide this necessary flexibility, the "N" flex links 314 lengthen on the outside of the bent stent 300 and shorten on the inside of the bent stent 300 as the stent 300 traverses through the lumen. This increased flexibility, while necessary to percutaneously deliver the stent 300 to its desired location, may also contribute to the foreshortening effect described earlier.

While a stent is deploying (opening), the stent's flex connectors start to stretch and compensate for the foreshortening. If this post-deployed lengthening of the flex connectors is not large enough (based for the most part upon balloon lengthening with increasing pressure), the flex connector expansion will not compensate for the initial foreshortening. Accordingly, in order to minimize foreshortening, a design that minimizes the axial compressibility of the flex connector, while minimizing the flex connector ultimate compressibility is desired.

Figure 6:
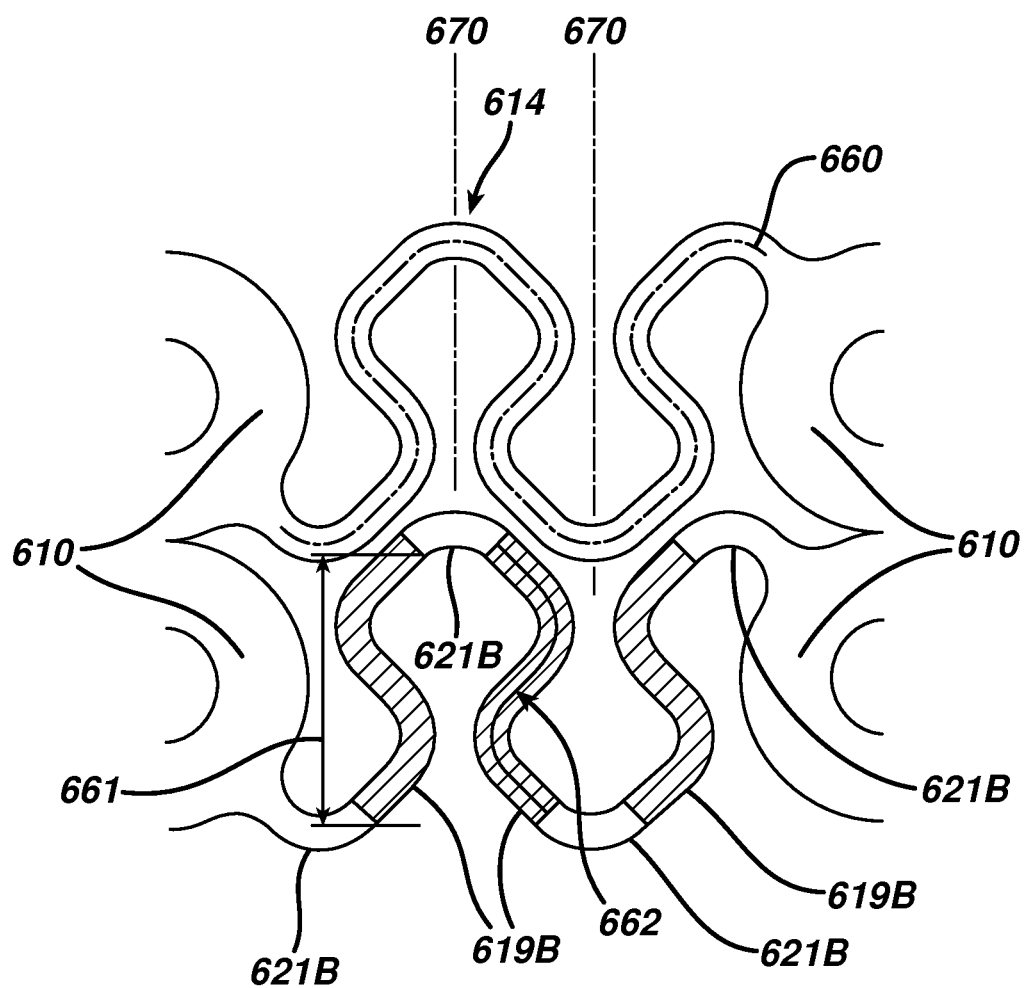
FIG. 6 illustrates a two-dimensional close-up view of a modified undulating flex link according to one embodiment of the present invention.

One embodiment of the present invention that minimizes the axial compressibility of a flex link during stent deployment is illustrated in FIG. 6. As can be seen from the figure, the modified N flex links 614 are illustrated in the pre-deployed crimped state, as they would appear if the stent were cut longitudinally and then laid out into a flat, 2-dimensional configuration. Although a modified "N" link is used for the purpose of example, one of ordinary skill in the art would understand that this invention applies equally to other flex link configurations, including modified "J" flex links.

Each "N" flex link 614 comprises four generally longitudinally extending curved segments 621(b) connected by three generally circumferentially undulating segments 619(b). The undulating segments 619(b) have a centerline length 662 and an overall length 661 as can be seen in FIG. 6. The centerline length is typically between approximately 5 and 25 percent greater than the overall length. As described earlier, the flex link 614 is connected to two curved loop members 610 of adjacent hoop sections 606 (not shown).

Similarly, a modified "J" flex link (not shown) would be comprised of two generally longitudinally extending curved segments (621(b) connected by a generally circumferentially undulating segment 619(b). The undulating segment 619(b) has a centerline length and an overall length similar to that shown in FIG. 6 for the modified "N" flex link. The centerline length is typically between approximately 5 and 25 percent greater than the overall length, preferably approximately 12 percent greater than the overall length.

Turning again to FIG. 6, it can be seen that the four longitudinally extending curved segments 621(b) are similar in shape and configuration to the segments 321(b) shown in the prior art stents illustrated in FIGS. 1 through 5. However, to minimize the axial compressibility of the flex link 614 during stent deployment, the generally circumferentially extending segments 319(b) of the prior art stents have been replaced with the circumferentially undulating element 619(b). The profile of the undulating elements 619(b) decreases the lateral distance the flex link 614 may compress during stent deployment by causing direct contact between adjacent undulating elements 619(b), or between the undulating element 619(b) and the adjacent loop member 610. However, it is preferred to maintain some gap between adjacent undulating elements 619(b), and between the loop members 610 and undulating elements 619(b) when the stent is being delivered to the deployment site in the crimped configuration.

In a preferred embodiment, the undulating elements 619(b) are arranged to be out-of-phase to each other. Phase may be defined as the angular relationship between each element. By way of example, each undulating element 619(b) in FIG. 6 is 180 degrees out-of-phase with the undulating element 619(b) either directly proceeding or following the element. That is to say, each undulating element is a mirror image reflection of the adjacent undulating element about reference line 670. Accordingly, adjacent elements are 180 degrees out-of-phase with each other, while every second undulating element are in phase with each other.

Although a phase shift of 180 degrees is shown for the purpose of example, one of ordinary skill in the art would appreciate that other degrees of phase shift may be used to achieve similar results.

As earlier disclosed, foreshortening occurs to varying degrees with all stents, determined predominately by how the particular stent design accommodates expansion. Stents deployed by standard catheter balloons invariably see the balloon inflate at the weakest section first, typically at the exposed distal and/or proximal ends. The inflated end(s) of the stent will experience the pressure of the balloon pressing outward in a radial direction to expand the stent, and also inwardly in an axial compressive direction. orienting adjacent undulating elements 619(b) 180 degrees out-of-phase from each other minimizes the lateral distance the flex link 614 can compress during stent deployment.

Figure 7A:
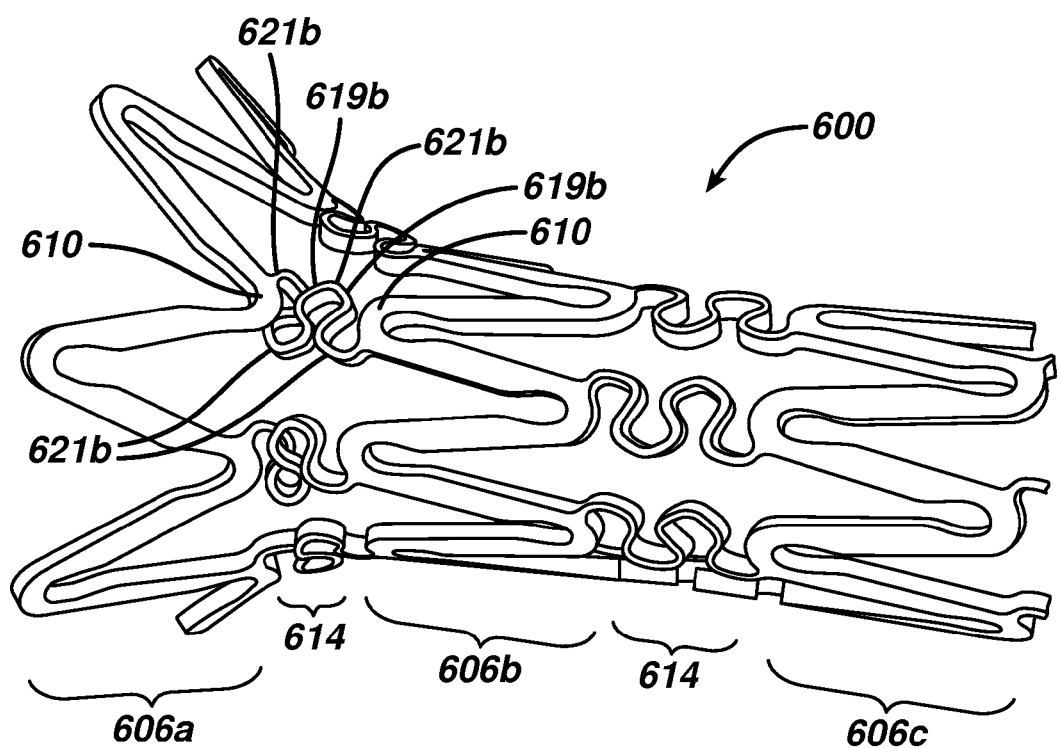
FIG. 7A is a perspective view of the proximal end of a stent during deployment according to one embodiment of the present invention.

FIG. 7A is a perspective view of the proximal end of a stent 600 being deployed. The stent 600 has undulating flex links 614 according to one embodiment of the present invention. As the balloon (not shown) begins to inflate, the proximal and distal end portions (only the proximal end portion is shown) start to expand before the remainder of the stent 600. As this inflation progresses, the flex connectors. 614 along the proximal end begins to compress until the adjacent undulating elements 619(b) contact one another. Similarly, the undulating elements 619(b) may contact the loop members 610 on the adjacent hoop sections 606 (606(a) and 606(b)). This contact between adjacent components substantially prohibits the lateral compression of the stent.

Figure 7B:
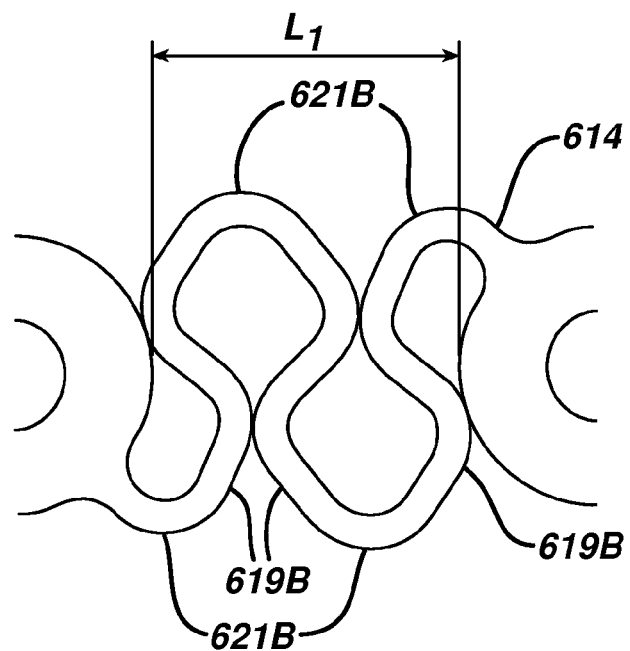
FIG. 7B illustrates a two-dimensional close-up view of the minimum compressed length of the modified undulating flex link according to one embodiment of the present invention.
Figure 7C:
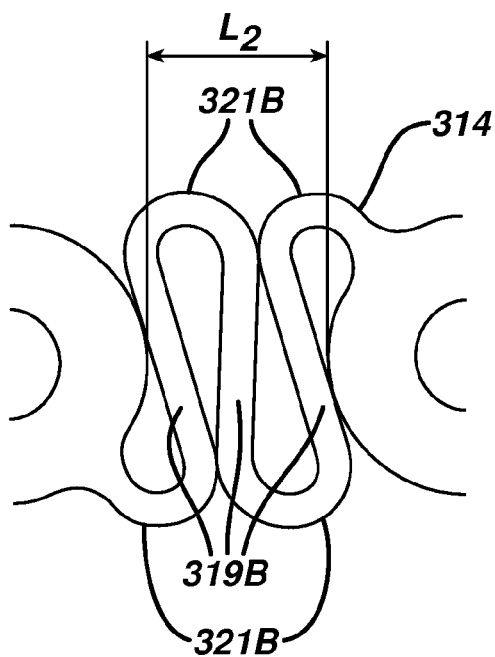
FIG. 7C illustrates a two-dimensional close-up view of the minimum compressed length of an exemplary "N" flex link.

FIGS. 7B and 7C illustrate the minimum compressed length (L) of the optimized and prior art flex links respectively during deployment (expansion) of the stent.

As can be seen in FIG. 7B, during expansion of the stent, the axial compression is driven by the ends of the balloon, and the flex link 614 is compressed until the undulating elements 619(b) contact each other. Once this position is reached, the flex link 614 has attained its minimum compressed length L1.

Similarly when the prior art stent depicted in FIG. 7C is expanded, the flex link 314 compresses. However, in the prior art stents, the geometry of the circumerentially extending segments 319(b) (being straight) allow greater compression of the flex link 314 until its minimum compressed length L2 is reached. As can be seen from the Figures, the minimum compressed length L1 of the flex link 614 is greater than the minimum compressed length L2 of prior art flex link 314.

An added feature of the design illustrated in FIG. 7A is that by reducing the lateral distance the flex link 614 can compress, the stress on the curved segments 621(b) is reduced.

Turning again to FIG. 6, the centerline length 660 of flex link 614 is shown. As described earlier, the centerline length of the flex link is proportional to the flex link's flexibility. In a preferred embodiment, the centerline length 660 of the flex link 614 is between 5 and 25 percent, preferably, approximately 12 percent greater than the centerline length 360 of the prior art flex link 314, thus providing increased flexibility of the flex link 614 while still minimizing the lateral distance the flex link 614 may compress during stent deployment.

While a number of variations of the invention have been shown and described in detail, other modifications and methods of use contemplated within the scope of this invention will be readily apparent to those of skill in the art based upon this disclosure. It is contemplated that various combinations or sub combinations of the specific embodiments may be made and still fall within the scope of the invention.

The following claims are provided to illustrate examples of some beneficial aspects of the subject matter disclosed herein which are within the scope of the present invention.

What is claimed is:

1. An intraluminal prosthetic device comprising:
   a first hoop section having a cylindrical shape with a longitudinal axis and a circumference, the cylindrical shape defining a longitudinal direction generally oriented along the longitudinal axis and a circumferential direction generally oriented along the circumference when the intraluminal prosthetic device is cut longitudinally and laid out flat in a 2-dimensional configuration, wherein the first hoop section comprises a plurality of longitudinally oriented struts connected by loop members having an outer radius;
   a second hoop section having a cylindrical shape and being axially aligned but longitudinally offset from the first hoop section along the longitudinal axis, wherein the second hoop section comprises a plurality of longitudinally oriented struts connected by loop members having an outer radius; and
   a plurality of flex members, each flex member having a first and a second end, wherein the first end of each flex member is attached to the first hoop section at the outer radius of a loop member and the second end of each flex member is attached to the second hoop section at the outer radius of a loop member, each flex member comprising at least two undulating segments that generally extend, end to end, in a circumferential direction, wherein the start and end points of each circumferentially extending undulating segment are longitudinally aligned with the corresponding start and end points of the immediately adjacent circumferentially extending undulating segment and wherein the start and end points of each circumferentially extending undulating segment are circumferentially aligned.

2. The intraluminal prosthetic device of claim 1 wherein the first and the second hoop sections comprise a plurality of longitudinally arranged strut members, and a plurality of loop members connecting the adjacent strut members.

3. The intraluminal prosthetic device of claim 2 wherein the longitudinally arranged struts are connected at opposite ends in a substantially "Z" shaped pattern.

4. The intraluminal prosthetic device of claim 2 wherein the first end of the flex member is attached to one loop on the first hoop section, and the second end of the flex member is attached to one loop on the second hoop section.

5. The intraluminal prosthetic device of claim 1 wherein the circumferentially undulating segment has a centerline length and an overall length, wherein the centerline length is between approximately five and twenty five percent greater that the overall length.

6. The intraluminal prosthetic device of claim 5 wherein the centerline length is approximately twelve percent greater that the overall length.

7. The intraluminal prosthetic device of claim 1 wherein, the flex member comprises a generally longitudinally extending curved segment directly connecting adjacent circumferentially extending undulating segments, end to end, when the intraluminal prosthetic device is cut longitudinally and laid out flat in a 2-dimensional configuration.

8. The intraluminal prosthetic device of claim 1 wherein the undulations in each circumferentially undulating segment are out of phase from the undulations in the immediately adjacent circumferentially undulating segment along the longitudinal axis.

9. An intraluminal prosthetic device comprising:
   a first hoop section having a cylindrical shape defining a longitudinal axis and a first circumference, wherein the first hoop section comprises a plurality of longitudinally oriented struts connected by loop members having an outer radius;
   a second hoop section having a cylindrical shape oriented along the longitudinal axis and having a second circumference, the second hoop section being axially aligned but longitudinally offset from the first hoop section along the longitudinal axis, the cylindrical shape of the first and the second hoop sections defining a longitudinal direction generally oriented along the longitudinal axis and a circumferential direction generally oriented along the circumference when the intraluminal prosthetic device is cut longitudinally and laid out flat in a 2-dimensional configuration, wherein the second hoop section comprises a plurality of longitudinally oriented struts connected by loop members having an outer radius; and
   one or more flex members, wherein each flex member has opposing ends attached at the outer radius of loop members of the first and the second hoop section, and wherein each flex member comprises at least two undulating segments that extend, end to end, in a generally circumferential direction, wherein immediately adjacent circumferentially extending undulating segments are reflectionally symmetric about a circumferential plane normal to the longitudinal axis.

10. The intraluminal prosthetic device of claim 9 wherein the circumferentially extending undulating segments have a centerline length and an overall length, wherein the centerline length is between approximately five and twenty five percent greater that the overall length.

11. The intraluminal prosthetic device of claim 9 wherein, the flex member comprises a generally longitudinally extending curved segment directly connecting adjacent circumferentially extending undulating segments, end to end, when the intraluminal prosthetic device is cut longitudinally and laid out flat in a 2-dimensional configuration.

12. An intraluminal prosthetic device comprising:
   a first hoop section;
   a second hoop section;
   one or more flex members attached between the first and the second hoop section, wherein each flex member comprises generally longitudinally extending curved segments directly connected end to end by generally circumferentially extending undulating segments when the intraluminal prosthetic device is cut longitudinally and laid out flat in a 2-dimensional configuration, each generally circumferentially extending undulating segment having substantially equal centerline lengths and having an S-shaped configuration.

* * * * *